US008268364B1

(12) United States Patent
Davidson et al.

(10) Patent No.: US 8,268,364 B1
(45) Date of Patent: Sep. 18, 2012

(54) WATER BASED PAIN RELIEVING COMPOSITION

(75) Inventors: Ron Davidson, Moore, OK (US); Jennifer Ellis, Lawton, OK (US)

(73) Assignee: Mintiva Holdings LLC, Oklahoma City, OK (US)

( * ) Notice: Subject to any disclaimer, the term of this patent is extended or adjusted under 35 U.S.C. 154(b) by 103 days.

(21) Appl. No.: 12/709,062

(22) Filed: Feb. 19, 2010

(51) Int. Cl.
| | |
|---|---|
| *A61K 36/00* | (2006.01) |
| *A61K 36/38* | (2006.01) |
| *A61K 36/76* | (2006.01) |
| *A61K 36/886* | (2006.01) |
| *A61K 36/534* | (2006.01) |
| *A61K 36/63* | (2006.01) |

(52) U.S. Cl. ......... 424/725; 424/730; 424/744; 424/747
(58) Field of Classification Search .................. None
See application file for complete search history.

(56) References Cited

U.S. PATENT DOCUMENTS

| | | | | |
|---|---|---|---|---|
| 6,579,543 | B1 * | 6/2003 | McClung | 424/728 |
| 7,282,224 | B1 * | 10/2007 | Roederer | 424/725 |
| 2004/0247707 | A1 * | 12/2004 | Le Roy et al. | 424/735 |
| 2007/0184128 | A1 * | 8/2007 | Dreyer | 424/725 |
| 2007/0218149 | A1 * | 9/2007 | Blau | 424/756 |
| 2009/0098213 | A1 * | 4/2009 | Tran | 424/526 |
| 2009/0123504 | A1 * | 5/2009 | Feldkamp et al. | 424/402 |

OTHER PUBLICATIONS

Vafaei et al, Effect of hydro-alcoholic extract of Matricaria chamomilla on acute pain in mice: an interaction with opioidegic neurons, European journal of neurology 2005; 12 (suppl 2): 204.*

* cited by examiner

*Primary Examiner* — Qiuwen Mi

(57) ABSTRACT

Disclosed is a water based topical pain relieving composition that is substantially odorless and does not leave a greasy or oily residue behind. The water based topical pain relieving composition may be particularly useful in treating areas near the eyes or mucous membranes. In some embodiments the topical pain relieving composition may comprise a water based emulsion comprising an effective amount of an analgesic composition comprising trolamine salicylate and an inflammation reducing composition comprising effective amounts of *Anthemis Nobilis* (roman chamomile) extract, *Arnica Montana* flower extract, *Calendula Officinalis* (marygold) extract, *Centaurea Cyanus* (blue bottle) extract, inflammation reducing oil, *Hypericum Perforatum* (St. John's Wort) extract, *Matricaria Chamomilla* (Wild Chamomile) extract, methylsulfonylmethane (MSM), *Salix Alba* (willow) bark extract, sorbitol, *Tilia Sylvestris* (limetree) extract, and *aloe vera* concentrate.

14 Claims, No Drawings

WATER BASED PAIN RELIEVING COMPOSITION

BACKGROUND OF THE INVENTION

Topical pain relieving creams have been commercially available for some time. These topical creams are often used to treat sore muscles, pain associated with the joints of a body, arthritis and other similar conditions. Many of these topical creams are thick and have a heavy texture. Such creams typically take a considerable amount of rubbing and manipulating to work the cream into the skin to reach the desired area of treatment. Additionally, these creams often leave an oil residue on the surface of the skin leaving the skin feeling greasy, slippery, and wet until the material is either ultimately absorbed into the skin or is sufficiently rubbed off the surface of the skin. This oily residue remaining on the skin can provide an uncomfortable feeling for the person as well as get on clothing worn by the person. Depending upon the ingredients used in the cream, many topical pain relieving creams may have an unpleasant odor associated with typical ingredients such as menthol and capsaicin. These odors can irritate the eyes and/or mucous membranes.

Topical creams that are thick, heavy, leave behind an oily or greasy residue, and are irritating to the eyes and mucous membranes may be suitable for general use on extremities such at the legs and arms. However, there are certain times and conditions in which a topical pain relieving composition is desired to be applied in an area on or near the face. For example, temporomandibular joint dysfunction (TMD) causes a pain that is associated with acute or chronic inflammation of the temporomandibular joint (TMJ), which connects the mandible to the skull. To reduce the pain associated with TMJ pain, it is desirable to apply pain relieving material to this area around the temporomandibular joint which is in close proximity to the eyes and mucous membranes. Applying a topical creams to the facial area near the TMJ that can irritate the eyes and mucous membranes which can be very uncomfortable for the person. Further, because of the irritation to the eyes and mucous membranes, the person may elect not to apply the cream to the desired treatment area as often as necessary or may elect not apply the cream at all.

Further, pain relieving creams that are thick and have a heavy texture that are used on the facial area can block facial pores potentially leading to acne break outs or other facial skin conditions. Creams that leave behind a greasy or oily residue can also block facial pores leading to undesirable facial skin conditions. Moreover, and in particular with respect to people who wear facial make-up or cosmetics, the use of heavy, thick creams that leave behind a greasy or oily residue make it difficult to apply cosmetics to the facial areas treated by the cream.

SUMMARY OF THE INVENTION

Certain embodiments of the invention are directed to a topical pain relieving composition in the form a water-based gel or gelatinous cream that exhibits a light texture and does not leave behind a greasy residue. Certain embodiments of the invention provide a pain relieving composition particularly useful in treating areas or regions on or near the face of a person. Certain embodiments of the composition allow for the application of cosmetics even after the composition has been applied to the face. The composition is substantially odor free, except for the addition of any desired fragrances, making the composition particularly useful in areas near the eyes or mucous membranes.

The water based topical pain relieving composition provides for effective delivery of pain relieving components to the applied area. The composition may in the form of a water based gel or gelatinous cream that is an oil in water emulsion.

Embodiments of the invention may include a topical pain relieving composition comprising, a water based emulsion comprising an effective amount of an analgesic composition comprising trolamine salicylate, and an inflammation reducing composition comprising effective amounts of *Anthemis Nobilis* (roman chamomile) extract, *Arnica Montana* flower extract, *Calendula Officinalis* (marygold) extract, *Centaurea Cyanus* (blue bottle) extract, inflammation reducing oil, *Hypericum Perforatum* (St. John's Wort) extract, *Matricaria Chamomilla* (Wild Chamomile) extract, methylsulfonylmethane (MSM), *Salix Alba* (willow) bark extract, Sorbitol, *Tilia Sylvestris* (limetree) extract, and *aloe vera* concentrate.

Further embodiments may include a topical pain relieving composition comprising a water based emulsion comprising an effective amount of an analgesic composition comprising trolamine salicylate; an inflammation reducing composition comprising effective amounts of *Anthemis Nobilis* (roman chamomile) extract, *Arnica Montana* flower extract, *Calendula Officinalis* (marygold) extract, *Centaurea Cyanus* (blue bottle) extract, inflammation reducing oil, *Hypericum Perforatum* (St. John's Wort) extract, *Matricaria Chamomilla* (Wild Chamomile) extract, methylsulfonylmethane (MSM), *Salix Alba* (willow) bark extract, Sorbitol, *Tilia Sylvestris* (limetree) extract, and *aloe vera* concentrate; *Mentha Piperita* (peppermint) leaf oil in an amount up to about 1% of the topical pain relieving composition; Carbopol 940 in an amount ranging from about 20% to about 25% of the pain relieving composition; triethanolamine in an amount ranging from about 0.5% to about 1.5% of the pain relieving composition; and water in an amount ranging from about 10% to about 15% of the pain relieving composition, wherein the pain relieving composition exhibits a viscosity ranging from about 11,000 centipoises to about 13,000 centipoises.

DETAILED DESCRIPTION OF EMBODIMENTS OF THE INVENTION

The following detailed description is intended as a description of exemplary embodiments of a water based pain relieving composition and is not intended to represent the only forms in which the exemplary embodiments may be constructed or used. The description sets forth the functions and steps for preparing and using the exemplary embodiments of the water based pain relieving composition. It is to be understood that the same or equivalent functions and steps which may be accomplished by different exemplary methods are also intended to be encompassed within the spirit and scope of the invention.

As used herein, "effective amount" means a sufficient amount of a compound, composition or other material described by this phrase to significantly induce a positive modification in the condition being treated, but low enough to avoid undue side effects (e.g., significant skin irritation or sensitization), within the scope of sound judgment of one skilled in the art. The effective amount of the compound, composition or other material may vary with the particular person being treated, factoring the age and physical condition of the person being treated, the severity of the condition, the duration of treatment, the nature of concurrent therapy, the specific compound, composition, or other material employed, the particular carrier utilized, and other factors within the knowledge and expertise of one skilled in the art.

As used herein, stated percentages of components, compositions, compounds are percentages by weight of the pain relieving composition.

A pain relieving composition according to certain embodiments of the invention is a water-based gel or gelatinous cream which comprises an effective amount of an analgesic composition comprising trolamine salicylate in combination with an effective amount of an inflammation reducing composition.

The analgesic composition includes a substantially odor free compound and is effective in reducing or relieving pain in the muscles, ligaments, tendons, or joints. The pain relieving composition includes an analgesic composition, which includes trolamine salicylate. Trolamine salicylate is a topical analgesic that is substantially odor free in contrast to other topical analgesics such as menthol or capsaicin. Trolamine salicylate is commercially available as Neo Heliopan TS from Symrise GmBH. The pain relieving composition may include up to about 13% by weight trolamine salicylate. In some embodiments, the pain relieving composition may include trolamine salicylate in an amount ranging from about 1% to about 13%. In further embodiments, the pain relieving composition may include trolamine salicylate in an amount ranging from about 6% to about 12%. In certain embodiments, the pain relieving composition includes trolamine salicylate in an amount of about 10% by weight.

The effectiveness of the pain relieving composition is due in large part to the combination of the analgesic composition with the combination of components in the inflammation reducing composition. Together the analgesic composition comprising trolamine salicylate in combination with the components of the inflammation reducing composition provide a synergistic effect in terms of pain relieving effectiveness for the pain relieving composition.

The inflammation reducing composition comprises components which include *Anthemis Nobilis* (roman chamomile) extract, *Arnica Montana* flower extract, *Calendula Officinalis* (marygold) extract, *Centaurea Cyanus* (blue bottle) extract, inflammation reducing oil, *Hypericum Perforatum* (St. John's Wort) extract, *Matricaria Chamomilla* (Wild Chamomile) extract, methylsulfonylmethane (MSM), *Salix Alba* (willow) bark extract, Sorbitol, *Tilia Sylvestris* (limetree) extract, and whole leaf *aloe vera* concentrate.

*Anthemis Nobilis* (roman chamomile) extract acts to provide a soothing benefit to dry, sensitive skin. *Anthemis Nobilis* (roman chamomile) extract is present in an amount ranging from about 0.1% to about 0.3% of the pain relieving composition, and preferably in some embodiments about 0.2% of the pain relieving composition.

*Arnica Montana* flower extract provides purifying and anti-puffiness properties. *Arnica Montana* flower extract may be present in an amount ranging from about 1% to about 3% of the pain relieving composition, and preferably in some embodiments about 1.5% of the pain relieving composition.

*Calendula Officinalis* (marygold) extract provides a soothing feeling and benefit to the skin. *Calendula Officinalis* (marygold) extract is present in an amount ranging from about 0.1% to about 0.3% of the pain relieving composition, and preferably in some embodiments about 0.2% of the pain relieving composition.

*Centaurea Cyanus* (blue bottle) extract provides anti-puffiness properties. *Centaurea Cyanus* (blue bottle) extract is present in an amount ranging from about 0.1% to about 0.3% of the pain relieving composition, and preferably in some embodiments about 0.2% of the pain relieving composition.

The inflammation reducing oil is an oil that includes inflammation reducing properties. Examples of inflammation reducing oil, includes, but is not limited to, emu oil, olive oil, and other similar oil with inflammation reducing properties, as well as one or more combinations of these oils. The inflammation reducing oil is present in an amount ranging from about 4% to about 7% of the pain relieving composition, and preferably in some embodiments about 5% of the pain relieving composition. In some embodiments the inflammation reducing oil provides anti-inflammatory properties and is useful as carry agent while easily absorbed by the skin. Emu oil and olive oil may be used separately or in combination together as the inflammation reducing oil.

*Hypericum Perforatum* (St. John's Wort) extract exhibits astringent, antiseptic, and anti-inflammatory properties. It acts to tighten pores, firms and cleans the skin, regenerates cutaneous tissues, and helps skin restoration. *Hypericum Perforatum* (St. John's Wort) extract is present in an amount ranging from about 0.1% to about 0.3% of the pain relieving composition, and preferably in some embodiments about 0.2% of the pain relieving composition.

*Matricaria Chamomilla* (Wild Chamomile) extract helps reduce puffiness and is a gentle astringent. *Matricaria Chamomilla* (Wild Chamomile) extract is present in an amount ranging from about 0.1% to about 0.3% of the pain relieving composition, and preferably in some embodiments about 0.2% of the pain relieving composition.

Methylsulfonylmethane (MSM) is thought to provide anti-inflammatory properties as well as aid in penetration of the components through the skin. MSM is present in an amount ranging from about 7 to about 9% of the pain relieving composition, and in some embodiments preferably about 5% of the pain relieving composition.

*Salix Alba* (Willow) bark extract act to inhibit perspiration and is gentle and astringent. *Salix Alba* (Willow) bark extract is present in an amount ranging from about 1% to about 3% of the pain relieving composition, and preferably in some embodiments about 2% of the pain relieving composition.

Sorbitol is a soothing sweet humectant that imparts a velvety texture to the skin and helps to prevent skin dryness. Sorbitol is present in an amount ranging from about 2% to about 3% of the pain relieving composition, and preferably in some embodiments about 2% of the pain relieving composition.

*Tilia Sylvestris* (limetree) extract is an antioxidant and is present in an amount ranging from about 0.1% to about 0.3% of the pain relieving composition, and preferably in some embodiments about 0.2% of the pain relieving composition.

Whole leaf *aloe vera* concentrate enhances dermal absorption and acts as a carrying agent. It typically imparts a smooth, soft feeling to the skin. The whole leaf *aloe vera* concentrate is present in an amount ranging from about 2% to about 4% of the pain relieving composition, and preferably in some embodiments about 3% of the pain relieving composition.

In some embodiments, *Mentha Piperita* (peppermint) leaf oil may be used in the pain relieving composition. Peppermint oil has a cooling effect on the skin. If the pain relieving composition is to be used near the eyes or near mucous membranes, peppermint oil should be used in relative low amounts. For a pain relieving composition that is to be applied to or near the face, or as a facial cream, peppermint oil may be used in amounts up to about 0.3% without significantly irritating the eyes or mucous membranes. If the pain relieving composition is going to be used on area away from the eyes and mucous membranes, higher levels of peppermint oil may be used. In pain relieving compositions that will be applied to area away from the eyes and mucous membranes, peppermint oil may be used in amounts up to about 1%.

The pain relieving composition may be described as an oil-in-water emulsion that provides a water-based gel or gelatinous cream. To provide the water-based gel or gelatinous cream, Carbopol 940 (commercially available information) is utilized in the pain relieving composition. Carbopol 940 when combined with water forms a water-based gel or gelatinous medium. Ingredients, compounds, or components that are water soluble will dissolve in the water-based gel and insoluble or relatively insoluble ingredients, compounds, or components may be suspended within the water-based gel. In some embodiments, Carbopol 940 is present in an amount ranging from about 20% to about 25% of the pain relieving composition. In certain embodiments, the pain relieving composition includes about 22.5% Carbopol 940. Water, preferably purified water, is used in an amount ranging from about 10% to about 15% of the pain relieving composition.

Because Carbopol 940 is relatively acidic, an alkaline compound should be used to bring the pH of the pain relieving composition into the range of about 6.8 to about 7.2. One suitable alkaline compound is triethanolamine. Typically triethanolamine may be used in an amount ranging from about 0.5% to about 1.5% of the pain relieving composition. In preferred embodiments, triethanolamine is present in an amount of about 1.0% of the pain relieving composition. This amount of triethanolamine it typically enough to bring the overall pH of the pain relieving composition to within a pH of about 6.8 to about 7.2. More or less triethanolamine may be required depending on the exact formulation, but enough should be used to bring the pH of the pain relieving composition into the range of 6.8 to about 7.2. Triethanolamine has the additional benefit of helping to provide a creamy and stable emulsion.

In some embodiments, cetearyl alcohol may be used to help reduce surface tension and help suspend various ingredients, composition, or compounds in the emulsion. In certain embodiments, cetearyl alcohol may be used in an amount ranging from about 4% to about 7% of the pain relieving composition. In further embodiments, the pain relieving composition may include about 4% cetearyl alcohol. Further, cetyl alcohol may be used as an emulsion stabilizer. Cetyl alcohol has the added benefit as an emollient and imparts a velvet texture to the skin. In certain embodiments cetyl alcohol may be used in an amount ranging from about 4% to about 7% of the pain relieving composition. In further embodiments, the paint relieving composition may include about 5.5% cetyl alcohol.

In certain embodiments, the pain relieving composition may include sodium lauryl sulfate in amounts ranging from about 3% to about 5% of the pain relieving composition. Sodium lauryl sulfate is a mild, high foaming, and anionic cleanser.

If desired, preservatives may be present in the pain relieving composition. Suitable preservatives include diazolidinyl urea (commercially available as Germall II), methylparaben and propylparaben. In some embodiments, the pain relieving composition may include on or more or all three of the above suitable preservatives. In some embodiments, diazolidinyl urea may be present in the pain relieving composition in an amount up to about 0.3%, and preferably up to about 0.25%. In certain embodiments methylparaben may be present in the pain relieving composition in an amount up to about 0.2%. In additional embodiments, propylparaben may be present in the pain relieving composition in an amount up to about 0.1%.

Optionally, fragrance may be added to the pain relieving composition to provide a pleasant experience with respect to applying the pain relieving cream. If the pain relieving composition is to be applied to areas near the eyes or mucous membranes, the fragrance should not be irritating to the mucous membranes or eyes. In some embodiments fragrance, such as peach orchard perfume, may be present in an amount up to about 0.5% of the pain relieving composition.

Other benefiting compositions other than the composition described above may be utilized in the pain relieving composition including conditioning agents, skin protectants, antioxidants, viscosity modifying agents, film formers, emollients, surfactants, solubilizing agents, preservatives, fragrance, chelating agents, foaming or antifoaming agents, opacifying agents, stabilizing agents, pH adjustors, absorbents, anti-caking agents, slip modifiers, various solvents, solubilizing agents, denaturants, bulking agents, emulsion stabilizing agents, suspending agents, colorants, binders, condition agent-emollients, surfactant emulsifying agents, biological products, cosmetic soothing aids, and/or combination thereof provided that the other benefiting compositions do not significantly alter or change the effectiveness and benefits described above for the pain relieving composition.

As discussed above, the pain relieving composition may be described as an oil-in-water emulsion that provides a water-based gel or gelatinous cream. The preparation of the emulsion will be described with respect to exemplary embodiments of the invention.

A hot phase is prepared by charging a suitable vessel with purified water and heating the water to about 80-85° C. The *aloe vera* concentrate is added to the vessel and mixed thoroughly. Preservatives such as methylparaben and propylparaben may be added to the vessel and mixed until fully dissolved. To the hot solution, MSM, cetyl alcholo, and cetearyl alcohol are added and mixed until fully dissolved. Carbopol 940 is then added to the hot solution and mixed thoroughly while maintaining the temperature of the solution at about 80-85° C. The inflammation reducing oil and sorbitol are then added to the hot solution and mixed.

Next the *Anthemis Nobilis* (roman chamomile) extract, *Arnica Montana* flower extract, *Calendula Officinalis* (marygold) extract, *Centaurea Cyanus* (blue bottle) extract, *Hypericum Perforatum* (St. John's Wort) extract, *Matricaria Chamomilla* (Wild Chamomile) extract, *Salix Alba* (willow) bark extract, and *Tilia Sylvestris* (limetree) extract are added to the solution and mixed while maintaining the temperature at about 80-85° C. If utilized, sodium lauryl sulfate is added to the hot solution with mixing until the solution becomes uniform. At this point the solution is cooled to about 20-25° C. with continuous mixing to provide a cool phase.

Once the solution cools to 20-25° C. certain components may be added to the cool phase. Triethanolamine is added to the cool phase and mixed until the solution becomes uniform. The solution may be opaque at this point in the process. Troamine salicylate is added to the cool phase with continued mixing. Any optional fragrances may be added and if peppermint oil used, it may be added to the cool phase while mixing the cool phase solution. Diazolidinyl urea (Germall II) if used as a preservative, maybe added to purified or deionized water and then added to the cool phase and mixed to provide a uniform consistency.

The resulting water based pain relieving composition is an oil in water emulsion that is essentially a water based gel or gelatinous cream. The pH of the water based pain relieving composition is preferably between about 6.8 and about 7.2. In some embodiments, the pain relieving composition has a viscosity ranging from about 11,000 centipoises to about 13,000 centipoises.

The resulting water based pain relieving composition containing no peppermint oil or very minor amounts of peppermint oil in the preparation may be used in areas near the eyes and mucous membranes. This water based pain relieving composition is substantially odor free and will not significantly block or clog facial pores. Further, the composition does not leave a greasy or oily residue on the skin allowing for the application of cosmetics after the water base pain relieving composition is applied. This composition is particularly useful for people experiencing discomfort from TMJ. The water based composition may be applied to the desired area by rubbing over the area to be treated. The combination of the analgesic composition comprising trolamine salicylate with the combination of components in the inflammation reducing composition provide effective delivery of ingredients to the area to be treated and provide a synergistic and beneficial effect in terms of pain relieving effectiveness.

EXAMPLE 1

Water Based Pain Relieving Composition Preparation 18 gallons of purified water was charged into a mixing vessel. The mixer was allowed to give a slow roll at the surface of the water. The water was heated to a temperature between 80-85° C. while maintaining mixing. The following ingredients were added to the heated water solution while maintaining the temperature between 80-85° C. and maintaining mixing: 0.25 kg of *aloe vera* concentrate; 0.51 kg of methylparaben; 0.25 kg of propylparaben; 0.5 kg of MSM, 13.97 kg of cetyl alcohol; 7.62 kg of cetearyl alcohol; 101.6 kg of carbopol 940; 12.7 kg of emu oil; 1.78 kg of Sorbitol; 0.003 kg of a combination of *Anthemis Nobilis* (roman chamomile) extract, *Calendula Officinalis* (marygold) extract, *Centaurea Cyanus* (blue bottle) extract, *Hypericum Perforatum* (St. John's Wort) extract, *Matricaria Chamomilla* (Wild Chamomile) extract, an *Tilia Sylvestris* (limetree) extract; 0.003 kg of *Salix Alba* (white willow) bark extract; 2.54 kg of *Arnica Montana* flower extract; and 4.45 kg of sodium lauryl sulfate.

The solution was cooled from 80-85° C. to 20-25° C. while mixing. When the solution reached a temperature of 20-25° C., the following ingredients were added while mixing: 3.3 kg of triethanolamine; 31.75 kg of trolamine salicylate; 1.27 kg of aromatic peach orchard perfume; 1.02 kg peppermint oil perfume or Mentha Piperita (peppermint) leaf oil. 0.64 kg of Diazolidinyl urea (Germall II) was added to 0.3 gallons of purified deionized water and added to the cooled solution with continued mixing.

The resulting composition was a water based pain relieving composition exhibiting a pH between 6.8 and 7.2 and a viscosity ranging from about 11,000 centipoises to about 13,000 centipoises.

EXAMPLE 2

Use of the Water Based Pain Relieving Composition

The water based pain relieving composition prepared in Example 1 was provided to patients with the primary complaint of Temporomandibular Joint pain.

Eighty consecutive patients with the primary complaint of Temporomandibular Joint (TMJ) pain were enrolled in a study to assess their response to interceptive provisional treatment between the time of their initial examination and the onset of their planned definitive treatment. Ten patients (12%) received no provisional treatment; eighteen patients (23%) received a mandibular soft splint cut away with a raised area over the first molar to function as a soft pivot splint referred to as a pain release splint; and fifty-two patients (65%) received the water based pain relieving composition prepared in Example 1.

These individuals were then sub-divided into groups of TMJ pain only, TMJ pain and otalgia, TMJ pain and swelling, TMJ pain and decreased range of motion (ROM) or TMJ pain, otalgia and decreased range of motion. Upon their return to the office to begin definitive treatment, their response to the provisional care protocols was evaluated. The ten patients (12%) who received no treatment had no improvement in their symptoms and some had worsened.

Eighteen (18) patients, or 23% of the total study population, received a pain release splint. Of this population, 28% reported no response. Among the 72% who did report relief of symptoms, results were evenly divided among mild, moderate and significant.

Fifty-two (52) patients, or 65% of the total study population, received the water based pain relieving composition. Of this population, two (2) patients (3%) did not use it and five (5) patients (10%) reported no relief. The remaining 87% of the patients using the topical cream reported results that were almost evenly divided among mild (31%), moderate (33%) and significant (23%).

One advantage of the home-applied cream was no in-office treatment time. 87% of the patients who applied the topical cream saw a clinically significant response, where the patients with the fabricated splint requiring impression technique, fabrication and insertion received 72% improvement. The topical water based pain relieving composition provided for immediate treatment of symptomatic patients and a greater degree of relief was provided by the water based pain relieving composition with the least clinical time spent to achieve the response.

While exemplary embodiments of the present invention have been described in detail above, the invention is intended to be limited only by the following claims.

What is claimed is:

1. A topical pain relieving composition comprising a water based emulsion comprising an effective amount of an analgesic composition comprising trolamine salicylate and an inflammation reducing composition comprising effective amounts of *Anthemis nobilis* extract, *Arnica montana* flower extract, *Calendula officinalis* extract, *Centaurea cyanus* extract, inflammation reducing oil, *Hypericum perforatum* extract, *Matricaria chamomilla* extract, methylsulfonylmethane, *Salix alba* bark extract, sorbitol, *Tilia sylvestris* extract, and *Aloe vera* concentrate.

2. The topical pain relieving composition of claim 1, wherein trolamine salicylate is in an amount ranging from about 1% to about 13% of the pain relieving composition.

3. The topical pain relieving composition of claim 1, wherein trolamine salicylate is in an amount ranging from about 6% to about 12% of the pain relieving composition.

4. The topical pain relieving composition of claim 1, wherein trolamine salicylate is in an amount of about 10% of the pain relieving composition.

5. The topical pain relieving composition of claim 1, wherein:
   trolamine salicylate is in an amount ranging from about 1% to about 13%;
   *Anthemis nobilis* extract is in an amount ranging from about 0.1% to about 0.3%;
   *Arnica montana* flower extract is in an amount ranging from about 1% to about 3%;
   *Calendula officinalis* extract is in an amount ranging from about 0.1% to about 0.3%;

*Centaurea cyanus* extract is in an amount ranging from about 0.1% to about 0.3%;

inflammation reducing oil is in an amount ranging from about 4% to about 7%;

*Hypericum perforatum* extract is in an amount ranging from about 0.1% to about 0.3%;

*Matricaria chamomilla* extract is in an amount ranging from about 0.1% to about 0.3%;

Methylsulfonylmethane is in an amount ranging from about 7 to about 9%;

*Salix alba* bark is in an amount ranging from about 1% to about 3%;

sorbitol is in an amount ranging from about 2% to about 3%;

*Tilia sylvestris* extract is present in an amount ranging from about 0.1% to about 0.3%; and

*Aloe vera* concentrate is in an amount ranging from about 2% to about 4% of the pain relieving composition.

6. The topical pain relieving composition of claim 1, further comprising *Mentha piperita* leaf oil in an amount up to about 0.3% of the topical pain relieving composition.

7. The topical pain relieving composition of claim 1, further comprising *Mentha piperita* leaf oil in an amount up to about 1% of the topical pain relieving composition.

8. The topical pain relieving composition of claim 1, further comprising carbopol 940 in an amount ranging from about 20% to about 25% of the pain relieving composition.

9. The topical pain relieving composition of claim 1, further comprising carbopol 940 in an amount ranging from about 20% to about 25% of the pain relieving composition and triethanolamine in an amount ranging from about 0.5% to about 1.5% of the pain relieving composition.

10. The topical pain relieving composition of claim 1, further comprising cetearyl alcohol in an amount ranging from about 4% to about 7% of the pain relieving composition, and cetyl alcohol in an amount ranging from about 4% to about 7% of the pain relieving composition.

11. The topical pain relieving composition of claim 1, wherein the inflammation reducing oil comprises emu oil.

12. The topical pain relieving composition of claim 1, wherein the inflammation reducing oil comprises olive oil.

13. The topical pain relieving composition of claim 1, wherein the inflammation reducing oil comprises olive oil and emu oil.

14. A topical pain relieving composition comprising:

a water based emulsion comprising an effective amount of an analgesic composition comprising trolamine salicylate;

an inflammation reducing composition comprising effective amounts of *Anthemis nobilis* extract, *Arnica montana* flower extract, *Calendula officinalis* extract, *Centaurea cyanus* extract, inflammation reducing oil, *Hypericum perforatum* extract, *Matricaria chamomilla* extract, methylsulfonylmethane, *Salix alba* bark extract, sorbitol, *Tilia sylvestris* extract, and *Aloe vera* concentrate;

*Mentha piperita* leaf oil in an amount up to about 1% of the topical pain relieving composition;

Carbopol 940 in an amount ranging from about 20% to about 25% of the pain relieving composition;

triethanolamine in an amount ranging from about 0.5% to about 1.5% of the pain relieving composition; and water in an amount ranging from about 10% to about 15% of the pain relieving composition, wherein the pain relieving composition exhibits a viscosity ranging from about 11,000 centipoises to about 13,000 centipoises.

* * * * *